United States Patent [19]

Ha et al.

[11] Patent Number: 5,779,863
[45] Date of Patent: Jul. 14, 1998

[54] PERFLUOROCOMPOUND SEPARATION AND PURIFICATION METHOD AND SYSTEM

[75] Inventors: Bao Ha, San Ramon; Timothy Arcuri, San Francisco, both of Calif.

[73] Assignees: Air Liquide America Corporation; Air Liquide Process and Construction, both of Houston, Tex.

[21] Appl. No.: 783,446

[22] Filed: Jan. 16, 1997

[51] Int. Cl.⁶ .................................................. B01D 3/00
[52] U.S. Cl. .................. 203/74; 202/172; 62/620; 62/630; 62/631; 570/178
[58] Field of Search .................. 62/620, 630, 631; 570/178; 203/74; 202/172

[56] References Cited

U.S. PATENT DOCUMENTS

| | | | |
|---|---|---|---|
| 4,177,196 | 12/1979 | Hildon et al. | 260/348.25 |
| 5,087,329 | 2/1992 | Felix | 203/67 |
| 5,334,787 | 8/1994 | Felix et al. | 570/169 |
| 5,399,549 | 3/1995 | Felix et al. | 570/169 |
| 5,421,964 | 6/1995 | Mahler et al. | 203/51 |
| 5,470,442 | 11/1995 | Mahler et al. | 203/56 |
| 5,502,969 | 4/1996 | Jin et al. | 62/11 |
| 5,523,499 | 6/1996 | Corbin et al. | 570/179 |
| 5,626,033 | 5/1997 | Tamhankar et al. | 62/617 |
| 5,639,355 | 6/1997 | Jongenburger | 203/78 |

FOREIGN PATENT DOCUMENTS 0 727 629  8/1996  European Pat. Off.

*Primary Examiner*—Nina Bhat
*Attorney, Agent, or Firm*—Burns, Doane, Swecker & Mathis, L.L.P.

[57] ABSTRACT

Provided is a novel method and system for separating and purifying perfluorocompounds (PFCs). The method comprises the steps of: (a) introducing a perfluorocompound-containing gas stream into a first distillation column; (b) removing a light product from the first column, and removing a heavy product from the first column; (c) introducing the first column light product into a second distillation column; (d) removing a light product from the second column, and removing a heavy product from the second column; (e) introducing the second column light product into a third distillation column; and (f) removing a light product from the third column, and removing a heavy product from the third column. The method and system can be advantageously used in the treatment of exhaust gases from semiconductor processing tools, and results in highly purified PFCs which can be recycled, thereby avoiding the release of PFCs into the atmosphere.

37 Claims, 4 Drawing Sheets

PERFLUOROCOMPOUND SEPARATION AND PURIFICATION METHOD AND SYSTEM

CROSS-REFERENCE TO RELATED APPLICATIONS

This application is related to assignee's copending application Ser. No. 08/783,941, attorney docket no. Serie 4030-CIP, filed on even date herewith, which is herein incorporated by reference.

BACKGROUND OF THE INVENTION

1. Field of the Invention

The present invention relates to a method for separating and purifying perfluorocompounds. The invention also relates to a system for separating and purifying perfluorocompounds. The inventive method and system have particular applicability in semiconductor manufacturing, for example, in the treatment of an exhaust gas from a semiconductor processing tool.

2. Description of the Related Art

In the semiconductor manufacturing industry, extensive use is made of perfluorocompounds (PFCs). For example, PFCs are required in various etching processes, such as oxide, metal and dielectric etching steps. In such processes, a gas or a plasma atmosphere selectively removes portions of a layer deposited on the substrate. Perfluorocompounds are also employed in deposition processes, such as silicon chemical vapor deposition (CVD), as well as in the cleaning of semiconductor processing chambers.

Perfluorocompound gases used in the above-mentioned processes include, for example, carbon tetrafluoride ($CF_4$), hexafluoroethane ($C_2F_6$), perafluoropropane ($C_3F_8$), trifluoromethane ($CHF_3$), sulfur hexafluoride ($SF_6$), nitrogen trifluoride ($NF_3$) and carbonyl fluoride ($COF_2$). Such gases can be used in either a pure or diluted form. Common carrier gases include air and inert gases, such as $N_2$, Ar, He and mixtures thereof. Perfluorocompounds can also be used in a mixture with other PFC gases.

When used in etching and cleaning processes, the PFCs generally do not completely react. As a result, unreacted PFCs may be present in the exhaust from the processing tool.

In addition to the substantial cost associated with the purchase of PFCS, it is well known and documented that PFCs are environmentally detrimental upon release into the atmosphere. In the Global Warming Symposium, Jun. 7–8, 1994, Dallas, Tex., $CF_4$, $C_2F_6$, $NF_3$ and $SF_6$ were identified as being greenhouse gases of particular concern in the semiconductor manufacturing industry.

In addition to replacing PFCs with other, less damaging materials, several methods for reducing the extent of PFC release into the atmosphere are known or are under development. For example, chemical-thermal decomposition of PFCs using various activated metals has been proposed. However, the spent bed materials must be disposed of, which itself can prove to be environmentally hazardous.

In the combustion-based decomposition process, i.e., chemical-thermal process, a flame supplies both the thermal energy and the reactants for decomposition of the PFCs. There are, however, some safety issues associated with the use of $H_2$ and natural gas fuels. Furthermore, assuming a sufficiently high temperature, all of the PFCs treated by this process will produce hydrofluoric acid (HF) as a combustion product. The emissions of HF are also of great concern and must themselves be treated. Furthermore, combustion processes undesirably produce $NO_x$, and $CO_2$.

Plasma-based decomposition has also been proposed as a method for treating PFCs. This process involves the generation of a plasma by, for example, an RF coupled system to partially decompose $C_2F_6$. While 90% decomposition of $C_2F_6$ is attainable, such systems are not yet commercially proven. Moreover, this decomposition process results in the generation of HF.

Methods in which PFCs are recovered, as opposed to being destroyed, are considered to be the most environmentally sound, since the PFCs can be reused. Such methods, therefore, are of great interest.

Perfluorocompound recovery based on combinations of adsorption or low temperature trapping has been proposed. These adsorption processes pose several problems, such as dealing with large amounts of $N_2$ associated with vacuum pump operation, the closeness in boiling points of $CF_4$ and $NF_3$, the mixing of various process streams, and the potential for reaction between the PFCs and the adsorbents.

In the article PFC Concentration and Recycle, presented at the Global Warming Symposium, the advantages of recovery processes which avoid the production of $CO_2$, $NO_x$ and HF are acknowledged. A process is disclosed which uses a dual bed adsorber with activated carbon. The PFCs are adsorbed on the carbon sieves while the "carrier" gas, e.g., $N_2$, $H_2$, is not adsorbed. One of the issues not yet resolved with such a system is that $CF_4$, which is non-polar, is not readily adsorbed by the carbon sieve. Moreover, a PFC purity higher than that achieved with such an adsorption unit is desired for reuse.

To meet the requirements of the semiconductor manufacturing industry and to overcome the disadvantages of the related art, it is an object of the present invention to provide a novel method for separating and purifying a mixture of perfluorocompounds, and in particular for treating an exhaust stream from a semiconductor processing tool. The product purities achieved according to the inventive process are such that the PFC products can be recycled. Consequently, the release of PFCs into the atmosphere and the environmental damage associated therewith can be avoided. Furthermore, the recovered PFCs can be recycled to the processing tool, which can result in substantial savings since lesser volumes of new materials would be required. The purified product can also be recycled to the purification system itself, which allows for control of the incoming gas composition as well as facilitating stable and reliable operation.

It is a further object of the present invention to provide a system for practicing the inventive method for separating and purifying perfluorocompounds, and in particular for treating an exhaust stream from a semiconductor processing tool.

Other objects and aspects of the present invention will become apparent to one of ordinary skill in the art upon review of the specification, drawings and claims appended hereto.

SUMMARY OF THE INVENTION

The foregoing objectives are met by the method and system of the present invention. According to a first aspect of the present invention, a novel method for recovering and purifying perfluorocompounds is provided. The method comprises the steps of:

(a) introducing a perfluorocompound-containing gas stream into a first distillation column;

(b) removing a light product from the first column, and removing a heavy product from the first column;

(c) introducing the first column light product into a second distillation column;

(d) removing a light product from the second column, and removing a heavy product from the second column;

(e) introducing the second column light product into a third distillation column; and (f) removing a light product from the third column, and removing a heavy product from the third column.

According to a second aspect of the invention, a system for recovering and purifying perfluorocompounds is provided. The system comprises:

(a) a first distillation column and a line connected to the first column for introducing a perfluorocompound-containing stream thereto, and a line for removing a heavy product from the first column;

(b) a second distillation column and a line connecting the first column with the second column for conveying a light product from the first column to the second column, and a line for removing a heavy product from the second column; and (c) a third distillation column and a line connecting the second column with the third column for conveying a light product from the second column to the third column, a line for removing a heavy product from the third column, and a line for removing a light product from the third column.

BRIEF DESCRIPTION OF THE DRAWINGS

The objects and advantages of the invention will become apparent from the following detailed description of the preferred embodiments thereof in connection with the accompanying drawings, in which like reference numerals designate like elements, and in which.

DETAILED DESCRIPTION OF THE PREFERRED EMBODIMENTS OF THE INVENTION

It has now surprisingly and unexpectedly been determined that perfluorocompounds (PFCs) present in an effluent gas stream, for example, from one or more semiconductor processing tools, can be recovered and purified in an effective manner. In the perfluorocompound purification process according to the invention, the exhaust from a semiconductor processing tool is separated into various components and purified. According to a preferred purification process, the end products include a pure $CF_4$ stream (less than about 10 ppm impurities), pure $C_2F_6$ (less than about 10 ppm impurities), a pure $N_2$ offgas stream in the ppm or sub-ppm range, and an $SF_6$ waste stream.

As used herein, the terms "perfluorocompound" and "PFC" are used interchangeably, and are defined as compounds comprising C, S and/or N atoms wherein all or all but one hydrogen have been replaced by fluorine. The most common PFCs include, but are not limited to, any of the following compounds: fully fluorinated hydrocarbons such as $CF_4$, $C_2F_6$, $C_3F_8$, $C_4F_{10}$, and other fluorinated compounds such as $CHF_3$, $SF_6$, and $NF_3$. PFCs may also include $BF_3$, $COF_2$, $F_2$, HF, $SiF_4$, $WF_6$, and $WOF_4$. Perfluorocompounds, however, do not include chlorofluorocarbons, or compounds comprising two hydrogen substituents or more.

Also as used herein, the term "heavy product" refers to a stream removed from a portion of the distillation column below a feed stage, which is not returned to the column. The heavy product can be in a gaseous and/or a liquid state, and is preferably removed from the bottom of the column.

Also as used herein, the term "light product" refers to a stream removed from a portion of the distillation column above a feed stage, which is not returned to the column as reflux. The light product can be in a gaseous and/or a liquid state, and is preferably removed from the top of the column.

The method and system of the invention will now be described generally with reference to FIG. 1, which illustrates a process flow according to a first embodiment of the invention.

Figure 1:
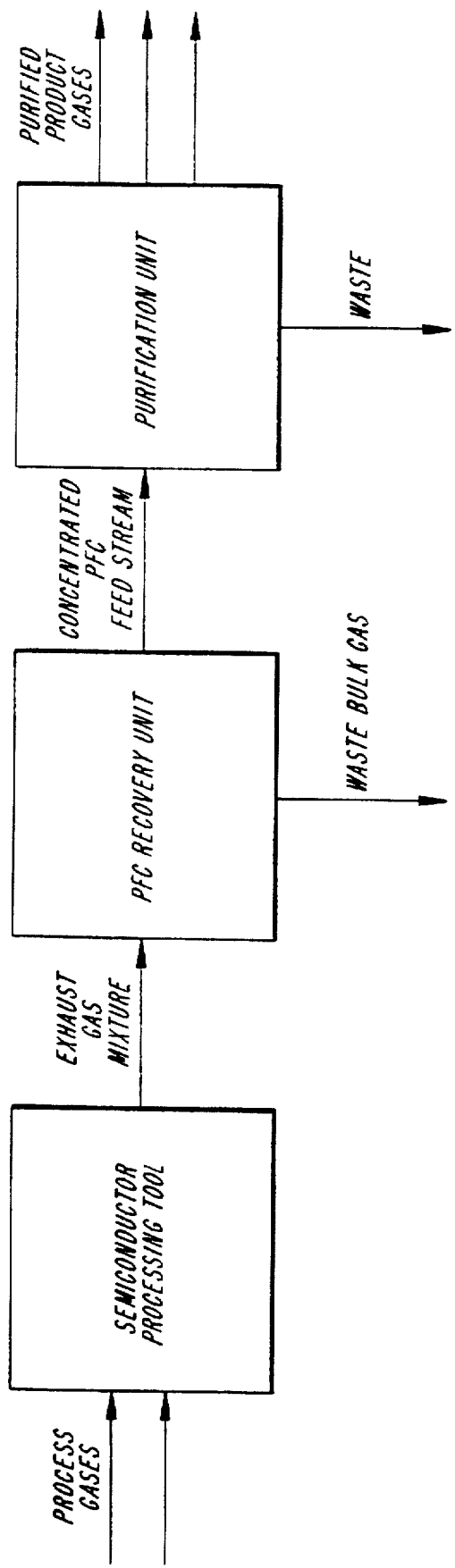
FIG. 1 illustrates a general process flow for recovering and purifying a gaseous effluent from a semiconductor processing tool.

With reference to FIG. 1, the process begins with an 10 exhaust gas mixture from a semiconductor processing tool, which may be any type of tool which uses or generates PFCs. The exhaust gas mixture, containing PFCs, carrier gases and any other process gases, is removed from the processing tool through an exhaust line. Prior to being introduced into the gas purification system, the gas mixture is preferably passed through a filter, and then compressed in a compressor. The compressed gas mixture is then optionally routed to a cooler or a heater to provide a desired temperature for the compressed gas mixture. The gas mixture is next preferably introduced into a dry scrubber and/or a wet scrubber to remove silicon hydrides, e.g., $NH_3$ and $AsH_3$, tetraethoxysilane (TEOS), halogens and halides. The exhaust stream can next be filtered to remove dust, particles, droplets, and the like, having sizes greater than, for example, 20 μm. Additionally, particles and dust may be removed in a filter upstream from the scrubber.

The exhaust stream is preferably passed through one or more systems to recover a majority of the PFCs while rejecting a majority of the carrier gases. Examples of suitable PFC recovery units are described in copending application Ser. No. 08/783,941, attorney docket no. Serie 4030-CIP, filed on even date herewith. As described in the copending application, the exhaust gas can be sent to a membrane unit through which the carrier gases of the mixture permeate, and are recovered or vented as a waste gas which can be purified and/or recycled according to known means. A concentrated PFC feed stream flows from the non-permeate side of the membrane unit.

This concentrated PFC feed stream is then introduced into a purification system, which produces purified product streams and waste streams. The PFC feed stream can be introduced to the purification system directly from the semiconductor processing tool or the recovery unit, or from a gas storage medium such as a cylinder, a bulk storage tank, or a tube trailer.

The inventive method and system are not limited in any way by the existence of any specific type of upstream system. Nor are the method and system limited to the treatment of any specific PFCs or PFC mixture. For purposes of discussion, a breakdown of the PFCs present in a typical PFC feed stream is as follows:

| | |
|---|---|
| $C_2F_6$ | 61.0 mol % |
| $CF_4$ | 30.0 mol % |
| $SF_6$ | 2.0 mol % |
| $NF_3$ | 1.5 mol % |
| $CHF_3$ | 0.5 mol % |
| $N_2$ | 5.0 mol % |

Figure 2:
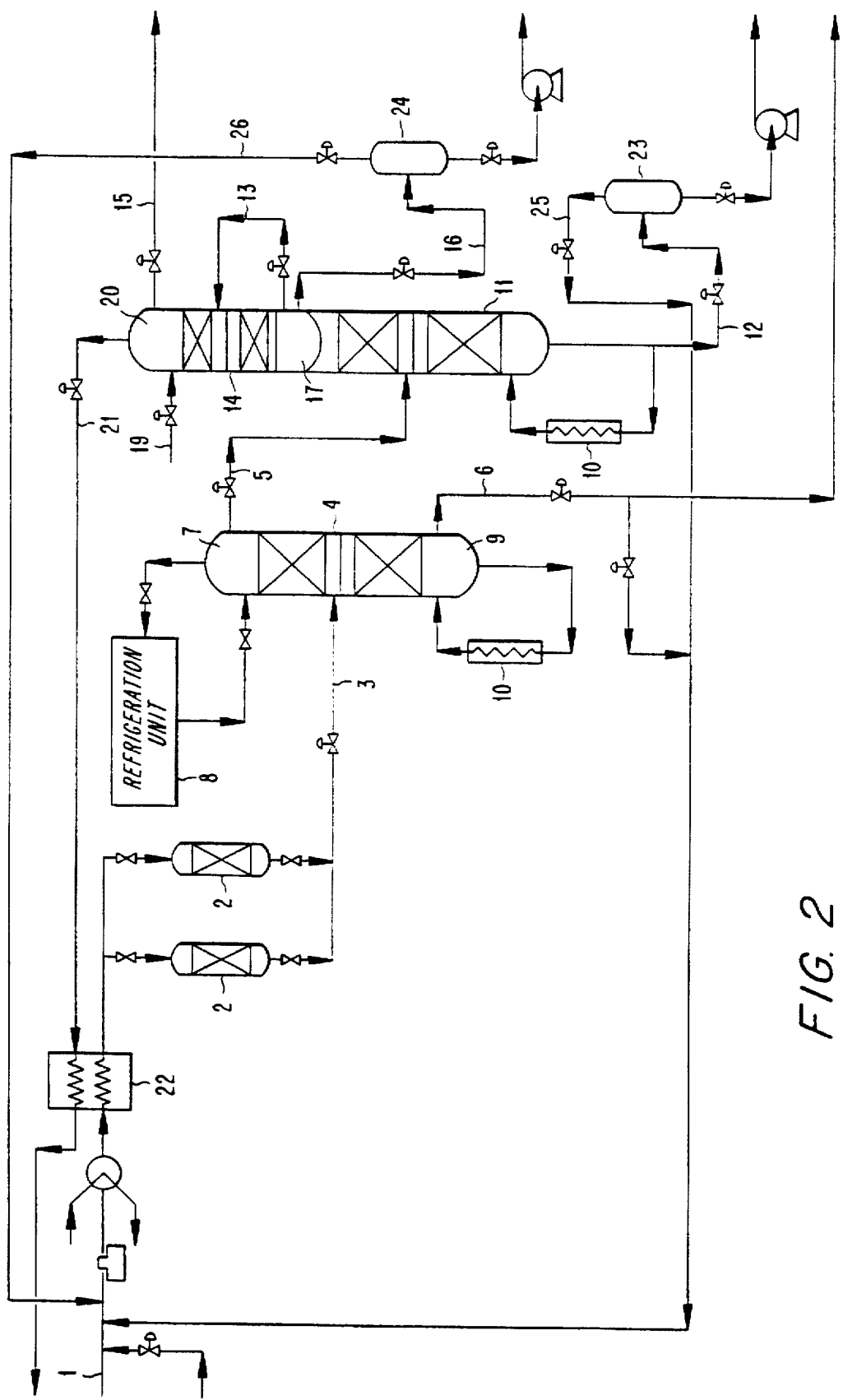
FIG. 2 is a process flow diagram for the perfluorocompound purification method and system according to a preferred embodiment of the invention.

With reference to FIG. 2, which shows the purification system in greater detail, concentrated PFC feed stream 1 from the recovery unit is compressed to a pressure lower than about 30 bar, preferably in the range of from about 5 to 15 bar, and more preferably from about 7 to 12 bar, and is cooled to a temperature in the range of from about $-120°$ to $-30°$ C., preferably from about $-30°$ to $-60°$ C., by, for example, a heat exchanger 24.

PFC feed stream 1 is then fed to one or more cold adsorption units 2 in which any existing impurities in the form of, for example, $CHF_3$, $C_2F_4$, and $NF_3$, are removed through cold adsorption. The non-adsorbed gas species in the effluent 3 from cold adsorption units 2 include, for example, $SF_6$, $C_2F_6$, $CF_4$ and $N_2$, and may include trace amounts of the aforementioned impurities, i.e., $CHF_3$, $C_2F_4$, and $NF_3$.

Suitable cold adsorption units 2 are known in the art, and are described, for example, in Perry's Chemical Engineers' Handbook. Suitable sorbent materials include, but are not limited to, 13X, 10X, 5A, 4A, 3A, Dowrex, PCB, and other ion exchanged zeolite adsorbents.

Adsorption unit effluent 3 is next fed to first cold distillation column 4, where effluent 3 is fractionated into light product 5 and heavy product 6. The $C_2F_6$, $CF_4$ and $N_2$ are removed in the light product 5, which ideally contains no more than 5 ppm of $SF_6$. Substantially all of the $SF_6$ introduced into first distillation column 4 is removed in heavy product 6. Heavy product 6 also includes those components which are heavier (i.e., higher-boiling) than $SF_6$ and may include some lighter (i.e., lower-boiling) components.

First column 4 operates at a pressure in the range of from about 5 to 15 bar, and a temperature in the range of from about $0°$ to $-90°$ C., preferably from about $-10°$ to $-45°$ C. Control of the pressure and temperature inside distillation columns is commonly understood by those skilled in the art.

The cooling duty for condenser 7 of first column 4 is provided by a refrigeration unit 8. The operational pressure of first column 4 is such that conventional refrigerants can be used in condenser 7. Suitable refrigerants are known to those skilled in the art, and include, for example, freons such as freon 22.

Means for providing the heat duty for the reboiler 9 of first column 4 are known in the art. For example, the heat duty can be provided by a heat source 10, such as an electric heater, an ambient vaporizer, or a heating medium stream, for example, a water stream.

Light product 5 from first distillation column 4 is fed to second distillation column 11, which is fractionated into heavy product 12 containing purified $C_2F_6$, and possibly containing impurities such as $CHF_3$, and light product 13 which includes $CF_4$ and $N_2$. Light product 13 may contain additional impurities, such as $NF_3$.

Second column 11 preferably operates at a pressure in the range of from about 5 to 12 bar and a temperature in the range of from about $0°$ to $-120°$ C., and more preferably from about $-25°$ to $-100°$ C.

Second column light product 13 is next fed to third distillation column 14, which is fractionated into a light product 15 and a heavy product 16. Light product 15 is $N_2$ gas, which may contain impurities, such as other air impurities. Purified $CF_4$ is removed as heavy product 16. This product may include impurities such as $NF_3$.

Third column 14 preferably operates at a pressure in the range of from about 1 to 10 bar and a temperature in the range of from about $-50°$ to $-200°$ C., more preferably from about $-90°$ to $-180°$ C.

Second distillation column 11 is preferably thermally linked with third distillation column 14 by a common reboiler/condenser arrangement. This thermal linkage utilizes the heating and/or cooling capacity of one or more streams or stream portions from one distillation column to provide reboiling and/or condensing duties, respectively, to another column.

Figure 3:
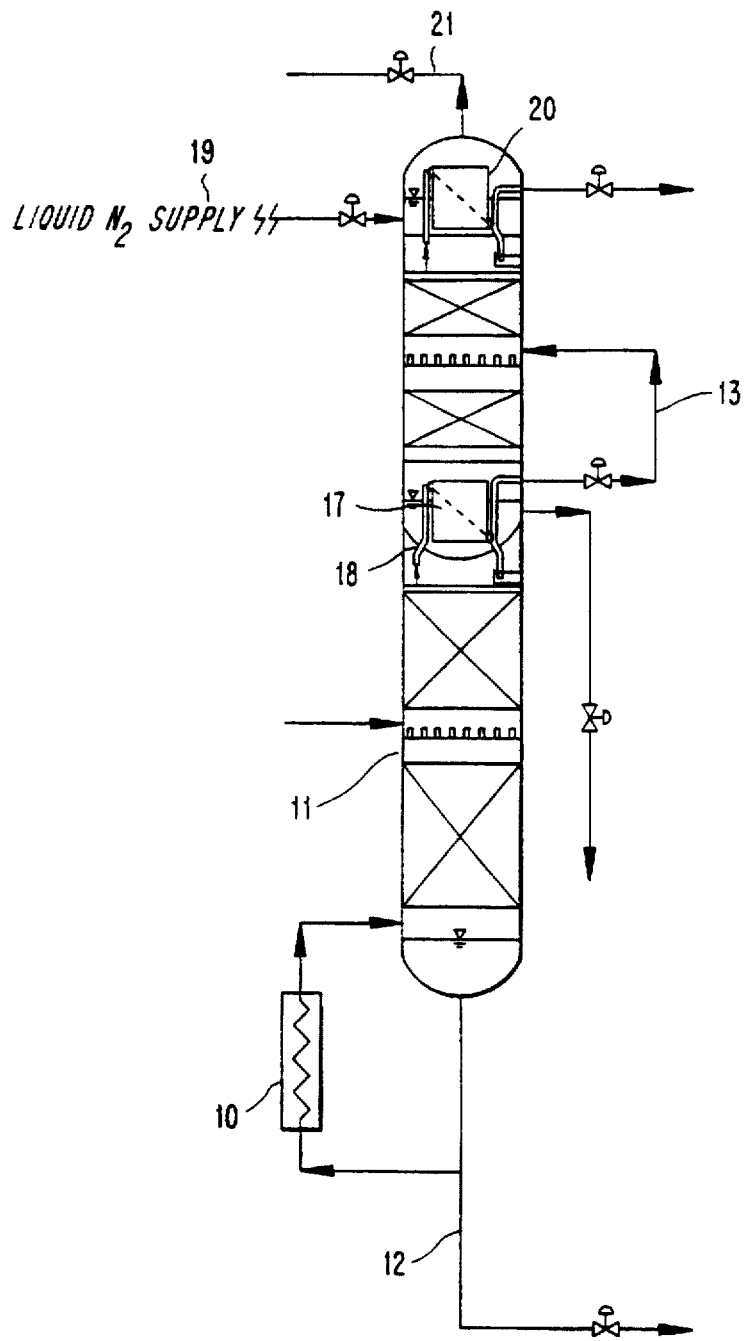
FIG. 3 illustrates two distillation columns which are stacked and thermally linked to each other which can be used in the method and system of the invention.

As shown in FIG. 3, the thermal linkage of columns 11 and 14 can be accomplished by physically stacking one column on top of the other column. The two columns can be contained in a single shell.

In this unique configuration, condenser 17 of second column 11 is at least partially immersed in the liquid at the bottom of third column 14. The vapor at the top of second column 11 is conveyed into third column 14 through condenser 17 via line 18. This vapor provides reboiling duty to third column 14 for vaporizing at least a portion of the liquid in the bottom of third column 14.

In the process of vaporizing the liquid in third column 14, heat is removed from the vapor in line 18 by the liquid in third column 14, resulting in at least partial condensation of the vapor in that line. From the condenser outlet, the condensed portion of the stream is returned to second column 11 as reflux. The vapor portion is introduced into an intermediate portion of the third column.

The thermal linkage can also be achieved by transporting, e.g., by pumping, either the liquid to be vaporized to the reboiler or the liquid reflux resulting from the condensation back to the column where the condensing vapor is originated. For example, it is additionally or alternatively possible for columns 11 and 14 to be located adjacent to each other, rather than being stacked.

In such a configuration, condenser 17 can be located external to the column, and the heavy liquid from column 14 can be conveyed to condenser 17, where it is partially vaporized by the warmer vapor from the top of second column 11. The resulting condensed portion of this stream is conveyed using a pump or other suitable mechanism back to column 11 as reflux. The vapor portion is introduced into the third column as in the previously described embodiment.

The pressures in second column 11 and third column 14 are controlled such that there is ample temperature driving force for the colder $CF_4$ containing liquid in the bottom of third column 14 to condense the light vapor of second column 11. Consequently, the need for an external source of refrigeration for the second column condenser 17 can be eliminated.

Liquid $N_2$ or another suitable cryogenic source 19 provides the refrigeration in the condenser 20 of third column 14, and is thus the only external source of refrigeration required by second and third columns 11 and 14 when such a thermally linked stacked column configuration is used. In providing cooling duty to the third column condenser 20, the liquid $N_2$ or suitable cryogen is vaporized in the process. The resulting cryogenic vapor stream 21 can be used to provide at least a portion of the cooling requirement in heat exchanger 22 for PFC feed stream 1. A liquid $N_2$ stream can also be injected as reflux liquid to the column thus economizing the reflux condenser.

The means for providing the heat duty for the reboiler of second column 11 can be the same as those specified above with reference to the first column, e.g., heat sources, such as an electric heater, an ambient vaporizer, or a heating medium stream, for example, a water stream.

Second and third column heavy product streams 12 and 16 can each be fed into a separate storage tank 23 and 24, respectively. A portion of the product is vaporized in each of tanks 23 and 24 as purified $C_2F_6$ and $CF_4$ vapor streams 25 and 26, respectively. At least portions of vapor streams 25 and 26 and first column heavy product 6, as well as any other product streams, can be recycled and combined with the PFC feed stream to control composition, and to dampen out any large fluctuations in the composition or flow of the feed. This pure product recycle is particularly advantageous to the process.

Figure 4:
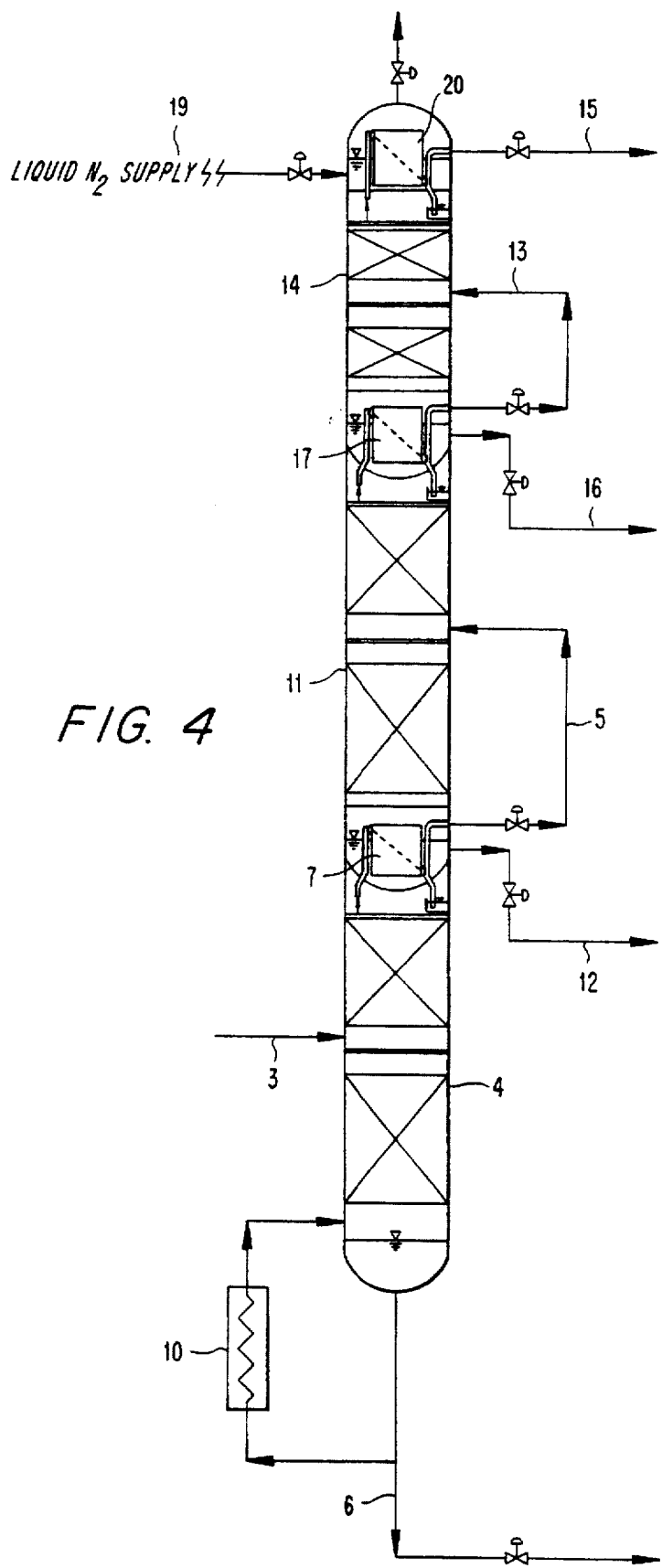
FIG. 4 illustrates three distillation columns which are stacked and thermally linked to each other which can be used in the method and system of the invention.

According to another embodiment of the invention, shown in FIG. 4, the first, second and third distillation columns 4, 11 and 14 can be stacked on top of and thermally linked with each other, in a manner similar to that described above with reference to the two-column structure. The columns can alternatively be disposed adjacent to each other while being thermally linked, as described above.

In this three column, stacked structure, first column 4 is preferably disposed on the bottom and third column 14 on top. Given this arrangement, the process can be controlled such that the condenser 7 of first column 4 provides reboil duty to second column 11, and the condenser 17 of second column 11 provides reboil duty to third column 14. This embodiment is particularly advantageous, since the only required source of refrigeration is liquid $N_2$, or some other suitable cryogenic source.

According to a further embodiment of the invention, a fourth distillation column can be provided to further purify heavy product 12, i.e., the $C_2F_6$ product, from second distillation column 11. In particular, use of a fourth distillation column allows for the removal of the remaining impurities, such as $CHF_3$, from second column heavy stream 12.

In yet another embodiment of the invention, one or more cold adsorption units can be added to remove remaining impurities such as $NF_3$ from the $CF_4$ heavy product of third column 14. Advantages of this embodiment include eliminating the possibility of co-adsorption and subsequent loss of a desired product, e.g., $C_2F_6$, with the impurities.

In another embodiment of the invention, cold adsorption units 2 can be moved to a position immediately downstream of first distillation column 4. In this case, light product 5 from the first distillation column is introduced to the adsorption units 2, with the resulting effluent stream being fed to second distillation column 11.

This configuration makes possible the elimination of the PFC-containing stream pre-cooling step prior to introduction into the first column. In such a case, the cryogenic source may be used elsewhere. Further advantages associated with this embodiment include a decrease in adsorption unit size due to the removal of heavy components such as $SF_6$ in first column 4 prior to adsorption. Additionally or alternatively, the adsorption can be performed at colder temperatures due to the elimination of such heavy components, which freeze at warmer temperatures.

Because the gas feed to the purification system can include recovered exhausts from multiple semiconductor processing tools and from multiple manufacturing sites, wide variations in feed gas composition are possible. By recycling the purified products to the purification system gas feed, an exceptional method for controlling the composition and flow rate of the feed stream is provided. This facilitates a stable and reliable operation of the purification system.

Additionally or alternatively, at least portions of one or more of the product streams can be recycled directly to the semiconductor processing tool, or packaged in suitable fashion for recycle and reuse in such tools. Considerable savings can result since the volume of fresh materials which must be purchased can be significantly reduced.

While the invention has been described in detail with reference to specific embodiments thereof, it will be apparent to those skilled in the art that various changes and modifications can be made, and equivalents employed, without departing from the scope of the appended claims.

What is claimed is:

1. A method for purifying perfluorocompounds, comprising the steps of:
   (a) introducing a perfluorocompound-containing gas stream into a first distillation column;
   (b) removing a light product from the first column, and removing a heavy product from the first column;
   (c) introducing the first column light product into a second distillation column;
   (d) removing a light product from the second column, and removing a heavy product from the second column;
   (e) introducing the second column light product into a third distillation column; and
   (f) removing a light product from the third column, and removing a heavy product from the third column;
   thereby obtaining a purified perfluorocompound.

2. The method according to claim 1, wherein the perfluorocompound-containing gas stream comprises $C_2F_6$ and $CF_4$.

3. The method according to claim 2, wherein the $C_2F_6$ is removed as the heavy product from the second column and the $CF_4$ is removed as the heavy product from the third column.

4. The method according to claim 3, wherein the second column heavy product contains $C_2F_6$, with less than about 10 ppm impurities.

5. The method according to claim 3, wherein the third column heavy product contains $CF_4$, with less than about 10 ppm impurities.

6. The method according to claim 3, wherein the second column heavy product contains $C_2F_6$, with less than about 10 ppm impurities, and the third column heavy product contains $CF_4$, with less than about 10 ppm impurities.

7. The method according to claim 2, wherein the perfluorocompound-containing gas stream further comprises $N_2$ and $SF_6$.

8. The method according to claim 7, wherein the $N_2$ is removed as the light product from the third column, and the $SF_6$ is removed as the heavy product from the first column.

9. The method according to claim 1, wherein the second and third columns are thermally linked together.

10. The method according to claim 9, wherein the second column and the third column are stacked on top of each other.

11. The method according to claim 10, wherein the third column is stacked on the second column.

12. The method according to claim 9, wherein the second column and the third column are contained in a single shell.

13. The method according to claim 9, wherein a liquid in the bottom portion of the third column condenses vapor from an upper portion of the second column.

14. The method according to claim 1, wherein the first, second and third columns are thermally linked together.

15. The method according to claim 1, wherein the first column operates at a pressure in the range of from about 5 to 15 bar, and at a temperature in the range of from about 0° to −90° C.

16. The method according to claim 1, wherein the second column operates at a pressure in the range of from about 5 to 12 bar, and at a temperature in the range of from about 0° to −120° C., and the third column operates at a pressure in the range of from about 1 to 10 bar, and at a temperature in the range of from about −50° to −200° C.

17. The method according to claim 16, wherein the second column operates at a temperature in the range of from about −25° to −100° C.

18. The method according to claim 16, wherein the third column operates at a temperature in the range of from about −90° to −180° C.

19. The method according to claim 1, further comprising introducing the second column heavy product into a fourth distillation column.

20. The method according to claim 1, wherein the perfluorocompound-containing gas stream is fed to a cold adsorption unit prior to being introduced into the first column.

21. The method according to claim 20, wherein the perfluorocompound-containing gas stream is cooled to a temperature in the range of from about −120° to −30° C. at or prior to being fed to the cold adsorption unit.

22. The method according to claim 1, further comprising recycling at least a portion of one or more of the product streams to a point upstream of the product streams.

23. The method according to claim 22, further comprising recycling at least a portion of one or more of the product streams to the perfluorocompound-containing stream.

24. The method according to claim 1, wherein the first column operates at a temperature in the range of from about 0° to −90° C., the second column operates at a temperature in the range of from about 0° to −120° C. and the third column operates at a temperature in the range of from about −50° to −200° C.

25. A method for purifying perfluorocompounds, comprising the steps of:

(a) introducing a perfluorocompound-containing gas stream comprising $C_2F_6$, $CF_4$, $N_2$ and $SF_6$ into a first distillation column;

(b) removing a light product comprising $C_2F_6$, $CF_4$ and $N_2$ from the first column, and removing a heavy product comprising $SF_6$ from the first column;

(c) introducing the first column light product into a second distillation column;

(d) removing a light product comprising $CF_4$ and $N_2$ from the second column, and removing a heavy product comprising $C_2F_6$ from the second column;

(e) introducing the second column light product into a third distillation column; and (f) removing a light product comprising $N_2$ from the third column, and removing a heavy product comprising $CF_4$ from the third column.

26. A system for purifying perfluorocompounds, comprising:

(a) a line connected to a source comprising perfluorocompounds which is connected to a first distillation column for introducing a perfluorocompound-containing stream thereto, and a line for removing a heavy product from the first column;

(b) a second distillation column and a line connecting the first column with the second column for conveying a light product from the first column to the second column, and a line for removing a heavy product from the second column; and (c) a third distillation column and a line connecting the second column with the third column for conveying a light product from the second column to the third column, a line for removing a heavy product from the third column, and a line for removing a light product from the third column.

27. The system according to claim 26, wherein the second and third columns are thermally linked together.

28. The system according to claim 27, wherein the second column and the third column are stacked on one another.

29. The system according to claim 28, wherein the third column is stacked on the second column.

30. The system according to claim 28, wherein the liquid from the bottom of the third column provides condensing duty in the second column, and the vapor in the second column provides reboiling duty in the third column.

31. The system according to claim 27, wherein the second column and the third column are contained in a single shell.

32. The system according to claim 27, wherein the first, second and third columns are thermally linked together.

33. The system according to claim 26, further comprising a line for introducing the second column heavy product into a fourth distillation column.

34. The system according to claim 26, further comprising a cold adsorption unit upstream from and in communication with the first column.

35. The system according to claim 34, further comprising means for cooling the feed to the cold absorption unit to a temperature in the range of from about −120° to −30° C.

36. The system according to claim 26, further comprising a line for recycling one or more of the product streams to a point upstream of the product streams.

37. The system according to claim 36, further comprising a line for recycling one or more of the product streams to a semiconductor processing tool.

* * * * *